(12) United States Patent
Jaeger (10) Patent No.: US 8,449,462 B2
(45) Date of Patent: May 28, 2013

(54) SPECULUM

(75) Inventor: John C. Jaeger, Oakfield, NY (US)

(73) Assignee: John C. Jaeger, Oakfield, NY (US)

( * ) Notice: Subject to any disclaimer, the term of this patent is extended or adjusted under 35 U.S.C. 154(b) by 0 days.

(21) Appl. No.: 13/253,237

(22) Filed: Oct. 5, 2011

(65) Prior Publication Data

US 2013/0090533 A1 Apr. 11, 2013

(51) Int. Cl.
*A61B 1/32* (2006.01)

(52) U.S. Cl.
USPC .......................................... 600/225; 600/224

(58) Field of Classification Search
USPC .................................................. 600/184–246
See application file for complete search history.

(56) References Cited

U.S. PATENT DOCUMENTS 5,916,151 A * 6/1999 Charters ....................... 600/224

* cited by examiner

*Primary Examiner* — Eduardo C Robert
*Assistant Examiner* — Christina Negrellirodriguez
(74) *Attorney, Agent, or Firm* — Novak Druce Connolley Bove + Quigg LLP (57) ABSTRACT

A speculum insertable into a body cavity of a person including a support member having an opening, provided with elongated arm sections each disposed in a plane including a centerline of such opening, blade members each lying in the plane of an arm section and having an intermediate section pivotally connected to the support member, a first end section displaceable into and out of engagement with the end section of another blade member and a second end section displaceable relative to one of the arm sections, means for releaseably biasing the first end sections of the blade members into engagement, permitting such end sections to be inserted into and removed from a body cavity, and means mounted on each arm member, engageable by a second end section of a blade member, for caroming such blade member to pivot about the axis thereof.

31 Claims, 6 Drawing Sheets

SPECULUM

This invention relates to a speculum and more particularly to an improved speculum which may be readily inserted into, manipulated upon being inserted into and removed from a body cavity of a person being examined by a physician.

BACKGROUND OF THE INVENTION

In the prior art, there has been developed a type of speculum which generally consists of an annular support member, and a set of circumferentially spaced blade members mounted on the support member, which can be pivoted together to permit the insertion of a set of ends of the blade members into a body cavity of a patient to be examined by a physician, pivoted apart upon insertion to enlarge such cavity for inspection of the interior thereof and pivoted together to permit retraction and removal of the ends of such blades upon completion of the examination. An example of such a speculum is illustrated and described in U.S. Pat. No. 7,798,960.

In the use of the type of speculum as described, it has been found to be greatly advantageous to improve upon the design of such instrument to render it more easy and economical to manufacture, more adaptive in use by an examining physician and more accommodating to a patient. Accordingly, it is the principal object of the present invention to provide a speculum of the type described which may be more easily and economically produced, more adaptive in use by an examining physician and most accommodating to a patient in terms of minimizing imposition and discomfort.

SUMMARY OF THE INVENTION

The principal object of the present invention is achieved by providing a speculum insertable into a body cavity of a person and expandable to enlarge such cavity for examination purposes, which generally includes a support member provided with an opening therethrough along a centerline thereof, provided with at least two elongated arm sections circumferentially spaced relative to such centerline, wherein each of such arm sections lies in a plane including such centerline, at least two blade members, each lying in the plane of such arm sections and having an intermediate section pivotally connected to such support member for pivotal movement of the blade, in such plane, a first end section angularly displaceable into and out of engagement with the end section of the other blade, a second end section angularly displacable toward and away from one of the arm sections, means for releasably biasing the first end sections of such blades into engagement, permitting such end sections to be inserted into and removed from such cavity and means mounted on each of the arm members and displaceable along a length thereof, engageable by a second end section of one of the blades, for camming such one blade to pivot it about the axis thereof, including means for releasably restraining the displacement of the camming means along the length of the arm member. In the preferred embodiment of the invention, the support member is annular, each of the arm sections is disposed at an angle relative to a plane disposed perpendicular relative to the centerline of the speculum, and the means for releasably restraining the camming means relative to the arm section comprises a leaf spring having a portion mounted on the camming means and a free end portion engaging the arm section.

DETAILED DESCRIPTION OF THE PREFERRED EMBODIMENTS OF THE INVENTION

Figure 1:
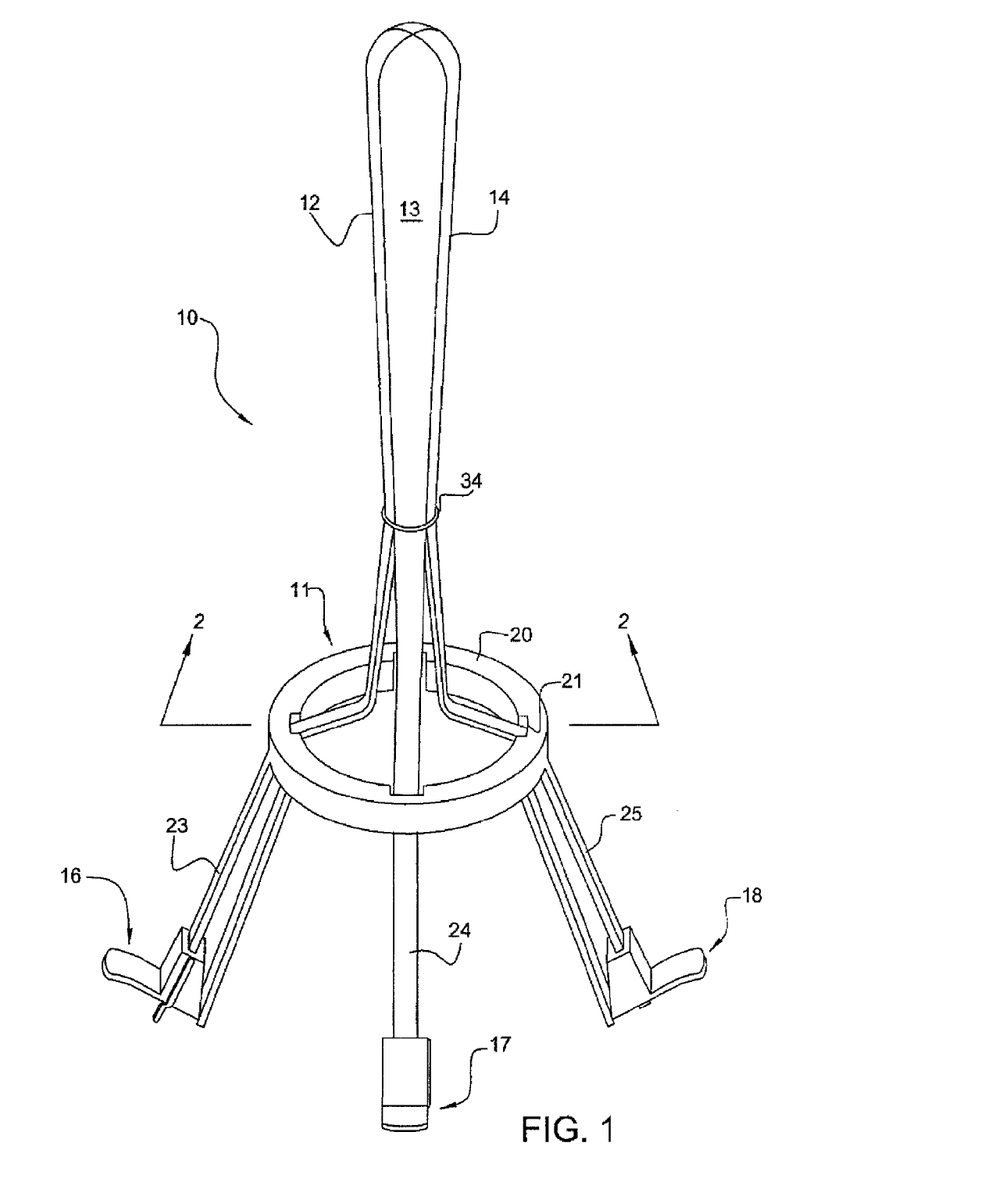
FIG. 1 is perspective view of an embodiment of the invention.
Figure 2:
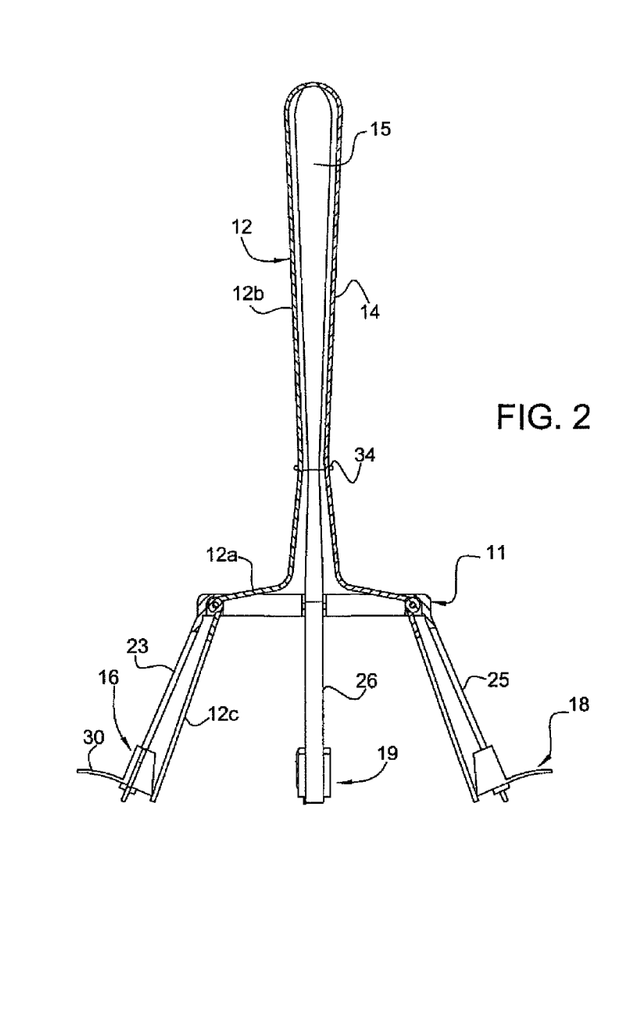
FIG. 2 is a view taken along line 2-2 in FIG. 1, illustrating first end sections of the blade members thereof in closed or retracted positions, interengaging.
Figure 3:
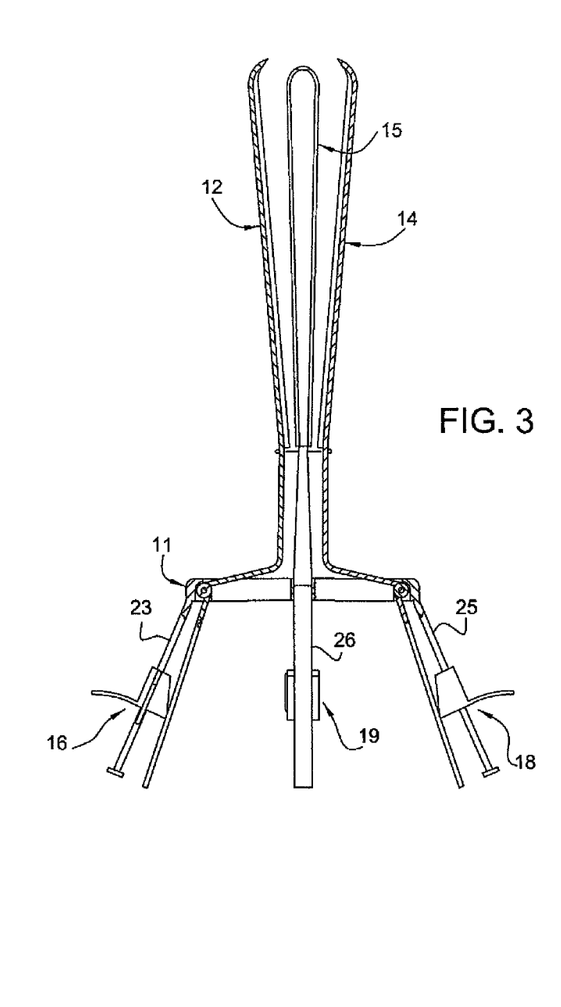
FIG. 3 is a view similar to the view shown in FIG. 2, illustrating the first end sections of the blade members in open or extended positions, spaced from each other.
Figure 4:
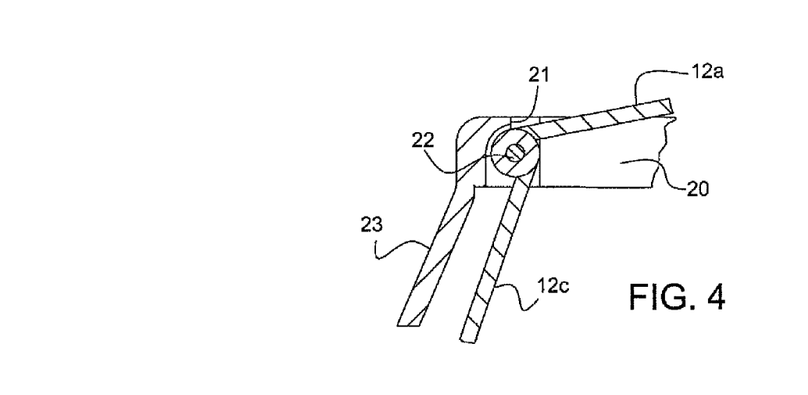
FIG. 4 is an enlarged, fractional view of a portion of the support member of the speculum, illustrating the manner in which a blade member is pivotally connected to the support member.

Referring to the drawings, there is illustrated a speculum 10 embodying the present invention which generally includes a support member 11, a set of substantially identical blade members 12 through 15 and a set of substantially identical cam members 16 through 19. Support member 11 includes an annular section 20 provided with a set of circumferentially spaced notches or recesses 21, relative to the centerline of annular section 20, each provided with a pin 22 as shown in FIG. 4, and a plurality of circumferentially spaced arms 23 through 26. Each of such arm sections lies in the plane of a blade member. Typically, blade member 12 includes an intermediate section 12a, a first end section 12b and a second end section 12c. As best seen in FIG. 4, intermediate blade section 12a is pivotally connected to pin 22 so that blade member 12 may be pivoted in the plane including arm section 23 and the centerline of annular section 20. First end section 12b of blade member 12 is disposed at an angle relative to intermediate section 12a and second end section 12c similarly is disposed at an angle relative intermediate section 12a and is disposable on an inner side of associated arm section 23, along the entire length thereof as shown in FIGS. 2 and 3. Each of the other blade members 24 through 26 is configured similarly to blade member 12, as described, and similarly is pivotally connected to the support member for pivotal movement in a plane including the centerline of annular section 20 and an associated arm section. First end section 12b of blade member 12 is provided with a surface arcuately configured in a plane disposed perpendicular relative to the centerline of the device when the four blade members are positioned together as shown in FIG. 1. The end portion of such first end section 12b forms a continuation of the arculately configured surface portion and has a configuration of a quadrant of a semisphere which when in the closed position as shown in FIG. 1 will cooperate with similar portions of the other blades to provide a rounded end provided with a semispherical surface merging with the actuate side surfaces of the other blade members when the blade members are in their closed, abutting positions.

Figure 5:
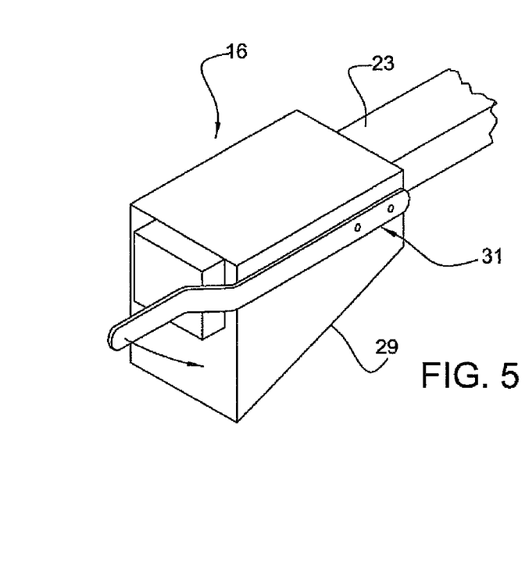
FIG. 5 is an enlarged, perspective view of a portion of an arm section of the support member of the speculum, illustrating a cam member thereof in a fully retracted position.
Figure 6:
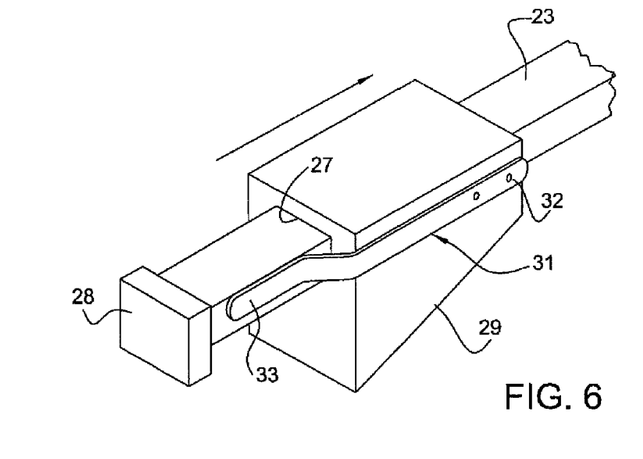
FIG. 6 is a view similar to the view shown in FIG. 5, illustrating the cam member displaced forwardly from the position thereof shown in FIG. 5.

Referring to FIGS. 5 and 6, cam member 16 is provided with an opening 27 therethrough which receives an arm section 23 therein to permit the cam member to displace along the length of the arm section. The rearward displacement of the cam member is limited by an abutment portion 28 formed on the end of the arm section which is engageable by the cam member. As best shown in FIGS. 2 and 3, an edge of underside 29 of the cam member engages second end section 12c of blade member 12 so that as the cam member is displaced along arm section 23, the cam member will engage such second end section to cause it to pivot about pivot pin 22. As such blade member pivots, it will be angularly displaced between a closed, retracted position as shown in FIG. 2 to an open position as shown in FIG. 3. The cam member may be displaced along the arm section simply by gripping the cam member with fingers and sliding it along the cam member which can be provided with a gripping portion 30 as shown in FIGS. 2 and 3. When cam member 16 is displaced to a certain position on the arm section to correspondingly angularly displace the first end portion of the blade member, it would be yieldably restrained in such position by a leaf spring 31 having a base section 32 secured to a side wall of the cam member and an end section 33 displaced relative to base section 32 and engaging a side surface of arm section 23. Each of cam members 17, 18 and 19 is similar to and functions in the same manner as described with the respect to cam member 16 to permit blade members 13, 14 and 15 to be angularly displaced.

In each of such arrangements of the blades and associated cam members, the pivotal connection of each of the blade member to the support member is sufficiently close to the base portion of the associated arm section, and the cam member has a sufficient maximum thickness so that when the cam member is displaced along the associated arm section, it will engage the associated second end section of the blade member to cause such blade member to pivot in the manner as previously described. Generally, the configurations of the blade members and the weight distribution of such members will cause the first end sections of such members to be retracted into closed positions as shown in FIG. 1 with the second end portions thereof biased against the inner sides of the cam members. To assure the bias of the first end sections of the blade members together as shown in FIG. 1, an elastomeric O-ring 34 may be provided about the first end sections of the blade members, adjacent the intermediate sections thereof as shown in FIGS. 2 and 3.

In the use of the speculum as described to enlarge a body cavity for examination purposes, the cam members are fully retracted to the positions shown in FIG. 2 to cause the first end portions of the blade members to retract and interengage as shown in FIG. 2. In such condition, the first end sections of the blade members provide a protruding portion having a smooth, semispherical end portion merging gradually into a rounded portion of diminishing diameter. Such protruding portion is inserted into the body cavity with the smooth surfaces thereof facilitating the insertion of the blade members in the closed condition, into the cavity. Once the protruding portion of the speculum has been inserted an intended distance within the cavity, one or more of the cam members may be gripped and displaced along an associated arm section thereof causing the selective blade member or members to pivot about its or their individual pivotal connection with the support member and correspondingly cause the first end sections thereof to spread apart as shown in FIG. 2. With the speculum in such an open or expanded condition, the physician may peer through the support member to examine the interior of the cavity which has been enlarged by reason of the expanded movement of the first end sections of the blade members against the walls of the cavity. Selective independent blades may be pivoted, all of the blades may be pivoted an equal amount and each of the blades may be pivoted different amounts, depending upon the nature of the examination. Once the examination has been completed, the speculum may be removed from the body cavity simply by gripping and displacing each of the cam members rearwardly into engagement with the abutment portion of the associated arm section causing the first end sections of the blade members to be angularly displaced into a retracted, closed condition, and withdrawing the inserted portion of the speculum from the body cavity. When the protruding portion of the speculum is inserted into the body cavity and the first end sections of the blade members have been angularly displaced to enlarge the cavity for viewing, such angularly displaced first end sections are maintained in their angularly displaced positions by leaf springs 31 which yieldably restrain the cam members engaging associated arm sections.

The various components of the speculum as described may be formed of any suitable materials including metallic and plastic materials having suitable properties compatible with the intended insertion of such devices into a body cavity. Preferably, the components of the speculum as described are formed of stainless steel with the outer surfaces of the first end sections of the blade members having smooth, curved surfaces merging with each other to provide a continuous surface thus permitting easy insertion and removal of the protruding portion of the speculum into and out of a body cavity with the least amount of discomfort to a patient. The speculum may be fabricated by simply forming the various components by stamping, casting or otherwise forming such components, pivotally connecting the blade members to the support member and mounting the cam members. Typically, the various components of the speculum will remain intact. However, such components may be easily disassembled, perhaps repaired, sterilized and reassembled for continued use.

The embodiment as described may be modified in several respects within the scope of the invention. The first end section of the blades may be configured in any manner to facilitate the insertion and removal of such sections in their contracted configuration without discomfort to the patent. The first end sections may be biased in the contracted condition by any means including coil springs provided at the pivotal connection of the blades to the support member. The support member may be of any configuration sufficient to permit the user to peer through such member and the retracted blade ends, to view the interior of the enlarged cavity. The arm members may be, formed integrally with the support member or connected thereto by other means. The blades may be individually or collectively pivotal. The cam member may be of any configuration, functional to react with the blades to pivot them, and the yieldable restraining means of the cam member may take any form.

Figure 7:
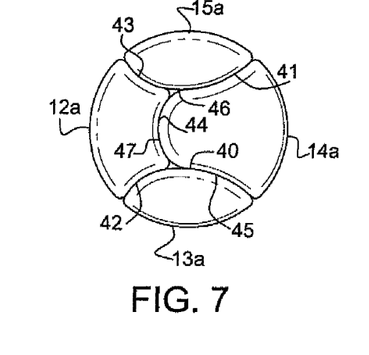
FIG. 7 is an enlarged top plan view of an alternate set of blade members, illustrated in a retracted or closed condition.
Figure 8:
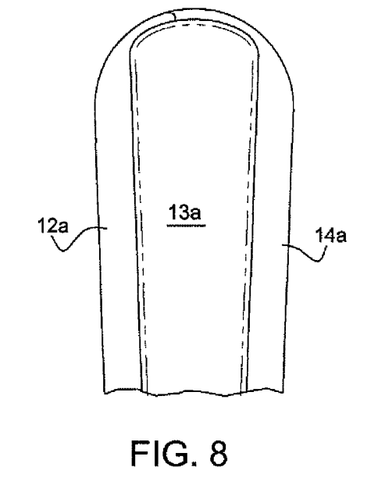
FIG. 8 is a side, partial view of the blade members shown in FIG. 7.
Figure 9:
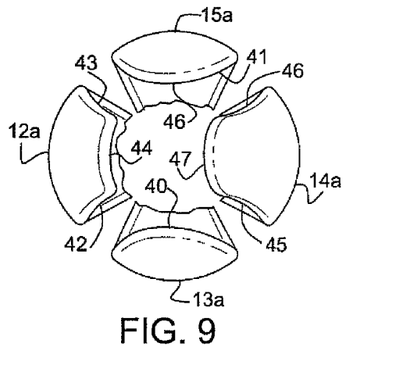
FIG. 9 is an enlarged top plan view of the set of blade members shown in FIG. 7, illustrated in an extended or open condition.
Figure 10:
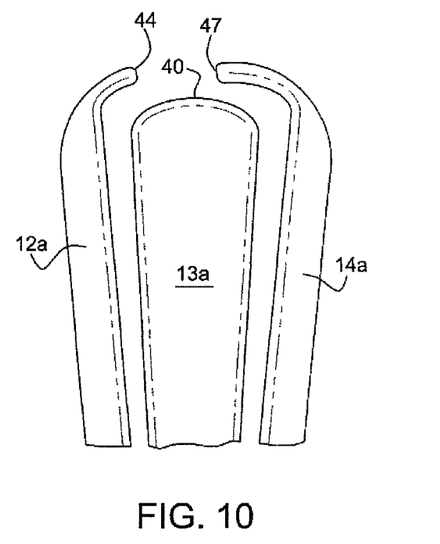
FIG. 10 is a side, partial view of the blade members shown in FIG. 9.

FIGS. 7 through 10 illustrate a variation of the configurations of the ends of the blade members. Blade members 12a, 13a, 14a and 15a corresponded to blade members 12, 13, 14 and 15, respectively, of the embodiment shown in FIGS. 1 through 3, with each being provided with an outer surface disposed arculately relative to the longitudinal centerline of such blade member when in the closed condition, and rounded edges. When in the closed position as shown in FIGS. 7 and 8, the free ends of blade members 13a and 15a are provided with protruding, rounded edges 40 and 41 spaced from the centerline of the blade members, the free end of blade member 12a is provided with recessed; rounded edges 42 and 43 which abut portions of edges 40 and 41 of blade members 13a and 15a and a recessed, rounded edge 44, and the free end of blade member 14a is provided with recessed, rounded edges 45 and 46 which abut edges 40 and 41, and a protruding, rounded edge 47 which abuts edge 44, to provide a closed, semispherical configuration with the end portion of blade member 14a extending across the centerline of the members.

Figure 11:
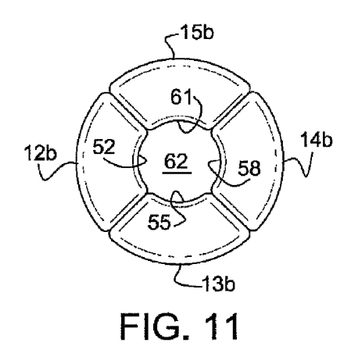
FIG. 11 is an enlarged top plan view of another alternate set of blade members, illustrated in a retracted or closed condition.
Figure 12:
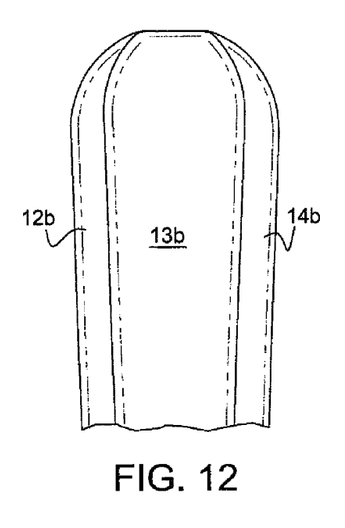
FIG. 12 is a side, partial view of the blade members shown in FIG. 11.
Figure 13:
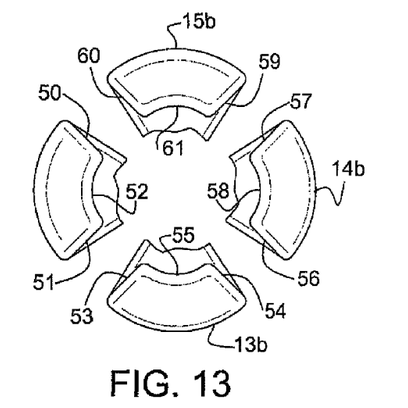
FIG. 13 is an enlarged top plan view of the set of blade members shown in FIG. 11, illustrated in the extended or open condition.
Figure 14:
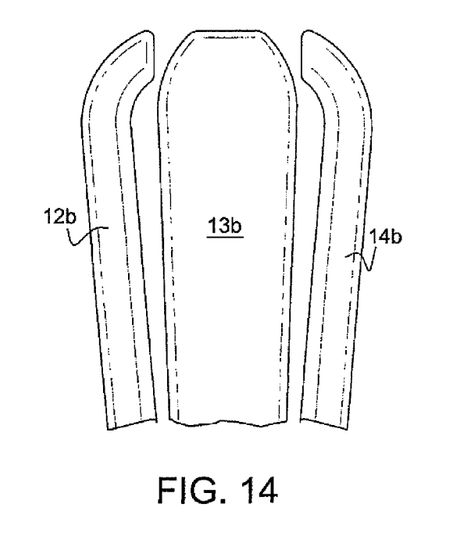
FIG. 14 is a side, partial view of the blades shown in FIG. 13.

FIGS. 11 through 14 illustrate another variation of the configurations of the blade members. Similar to the previously described variation, blade members 12b, 13b, 14b and 15b correspond to blade members 12, 13, 14 and 15, respectively, of the embodiment shown in FIGS. 1 through 3, with each being provided with an outer surface disposed arcuately relative to the longitudinal centerline of such blade member when in the closed condition, and rounded edges. When in the closed position as shown in FIGS. 11 and 12, the free end of blade member 12b is provided with converging side edges 50 and 51 and a recessed, rounded edge 52, the free end of blade member 13b is provided with converging side edges 53 which abuts side edge 51, and 54, and recessed, rounded edge 55, the free end of blade member 14b is provided with converging side edges 56 which abuts side edge 54 and 57, and recessed, rounded edge 58, which is spaced from edge 52 of member 12b, and the free end of blade member 15b is provided with converging side edge 50, which abuts edge 57 and 60 which abuts side edges 50 and recessed, rounded edge 61 which is spaced from opposed edge 55 of member 13b to provide an opening 62 along the centerline of the blades. In the closed condition, the ends of blade member 12b, 13b, 14b and 15b provide a rounded end portion with an opening in the center thereof.

Figure 15:
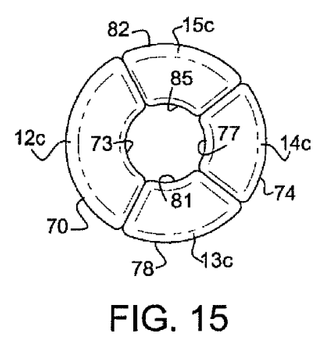
FIG. 15 is an enlarged top plan view of a still further alternate set of blade members, illustrated in a retracted or closed condition.

FIGS. 15 through 18 illustrate still another variation of the configurations of the end portions of the blade members. Similar to the previously described variations, blade members 12c, 13c, 14c and 15c correspond to blade members 12, 13, 14 and 15, respectively, of the embodiments shown in FIGS. 1 through 3, with each being provided with an outer surface disposed arculately relative to the longitudinal centerline of such blade member when in the closed condition, and rounded edges. Blade member 12c has a length greater than blade members 13c, 14c and 15c, an arcuate outer surface 70 relative to the longitudinal centerline of the blades, a pair on converging side edges 71 and 72 and a recessed, rounded edge 73. Blade member 14c is opposed to blade member 12c and includes an outer arcuate surface 74, a pair of converging edges 75 and 76 and a recessed, rounded edge 77. Blade member 13c includes an arcuate outer surface 78, a pair of converging side edges 79 and 80 which abut side edges 72 and 76 of blades 12c and 14c, respectively, when the blades are in the closed position as shown in FIG. 15 and a recessed, rounded edge 81. Blade member 15c is similar in configuration to blade member 13c and includes an arcuate outer surface 82 a pair of converging edges 83 and 84 which abut converging edges 71 and 75 of blade members 12c and 14c, respectively, when the blades are in a closed condition, and a recessed, rounded edge 85.

Figure 16:
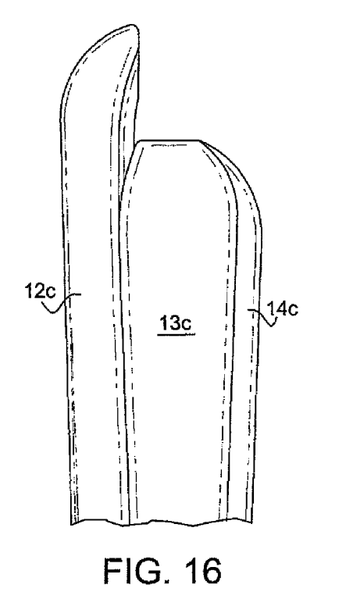
FIG. 16 is a side, partial view of the blade members shown in FIG. 15.

When the blades are in the closed condition as shown in FIGS. 15 and 16, portions of outer, arcuate surfaces 70, 78, 74 and 82 of the blades disposed in a plane disposed perpendicular longitudinal centerline of the blades, form a circle as best shown in FIG. 15. Similarly, recessed, rounded edges 81, 77 and 85 form a portion of a circle in a plane disposed perpendicular to the longitudinal centerline of the blades as shown in FIG. 15, further providing an opening along the centerline of the blade members.

Figure 17:
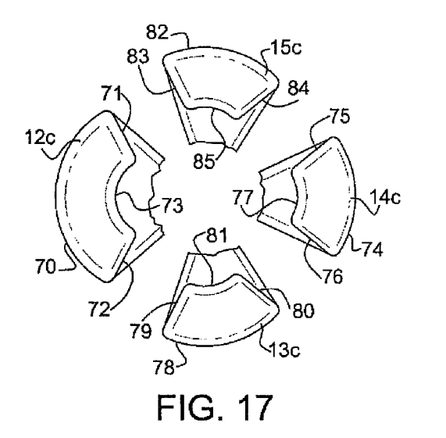
FIG. 17 is an enlarged top plan view of the set of blade members shown in FIG. 15, illustrated in the extended or open condition.
Figure 18:
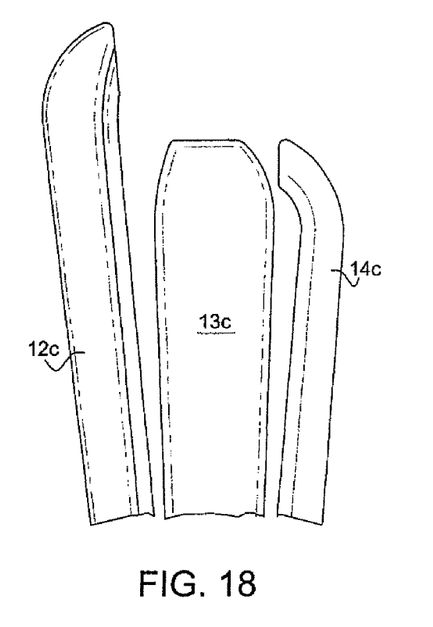
FIG. 18 is a side, partial view of the blades shown in FIG. 17.

When the blades are in the closed condition as shown in FIGS. 15 and 16, the length of the outer, arcuate surface 70 of blade member 12c, taken in plane disposed perpendicular to the centerline of the speculum and relevant to such centerline is no greater than 180°, the length of the outer, arcuate surface 74 in such plane and relative to the centerline is less than the length of outer, arcuate surface 70 and the length of each of the outer, arcuate surfaces 78 and 82 of blade members 13c and 15c, respectively, in such plane and relative to the centerline is less than the length of outer, arcuate surface 74. In such embodiment, the pivotal connections of the blades to annular section 20 of the support member are suitably circumferentially spaced to cause the blade members to pivot in planes including the centerline of the speculum between open and closed positions as illustrated in FIGS. 15 and 17. The configurations of ends of the blades of such embodiment facilitate the insertion and removal of the blades and the particular configuration of the end portion of blade member 12c permits the displacement of a selected portion of the cavity wall upon insertion of the blades into a cavity to more effectively configure the cavity opening to accommodate the examination procedure.

In each of the embodiments as described, with the blade members disposed in the retracted or closed condition, there is provided a configuration of spreadable blades that may be inserted into a body cavity without causing injury or discomfort to a patient. The rounded end of the closed blades, the rounded sides of the blade members and the rounded edges of the members greatly facilitate the insertion and removal of the instrument. Upon insertion of the instrument, portions of the cavity may be enlarged by pivoting any of the blade members independently or in concert with outer blade members. With the instrument inserted in a cavity with one or more of the blade members having been pivoted to enlarge one or more areas of the cavity, the rounded edges of the blade members allow the instrument to be displaced further into or toward the opening of the cavity to facilitate the examining procedure without causing any injury or discomfort to the patient.

From the foregoing detailed description, it will be evident that that are a number of changes, adaptations and modifications of the present invention, which come within the province of those persons having ordinary skill in the art to which the aforementioned invention pertains. However, it is intended that all such variations not departing from the spirit of the invention be considered as within the scope thereof as limited solely by the appended claims.

I claim:

1. A speculum insertable into a body cavity of a person and expandable to enlarge the opening of said cavity for examination purposes thereof, comprising:
   a support member provided with an opening therethrough along a centerline thereof, provided with at least two elongated arm sections circumferentially spaced relative to said centerline, wherein each of said arm sections lies in a plane including said centerline;
   at least two blade members, each lying in said plane of one of said arm sections and having an intermediate section pivotally connected to said support member for pivotal movement of said blade member in said plane, a first end section angularly displaceable into and out of engagement with an end section of said other blade member and a second end section angularly displaceable toward and away from one of said arm sections;
   means for releasably biasing said first end sections of said blade members into engagement, permitting said end sections thereof to be inserted into and removed from said cavity; and
   means mounted on each of said arm members and displaceable along a length thereof, engageable by a second end section of one of said blades, for camming said one blade to pivot about the axis thereof, including means for releasably restraining the displacement of said camming means along said length of said arm member.

2. A speculum according to claim 1 wherein said support member is annular.

3. A speculum according to claim 1 wherein each of said arm sections is displaced at an acute angle relative to a plane displaced perpendicular to said centerline.

4. A speculum according to claim 1 wherein said means for releasably restraining said camming means relative to said arm section comprises a leaf spring having a portion mounted on said camming means and a portion engaging said arm section providing a biasing force thereon.

5. A speculum according to claim 1 wherein said arm section includes an abutment engageable by said camming means.

6. A speculum according to claim 1 wherein said camming means is provided with an opening therethrough through which said arm section extends.

7. A speculum according to claim 1 wherein said camming means includes a projecting portion which may be gripped to displace said camming means along said arm member to pivot the associated blade member.

8. A speculum according to claim 1 wherein said camming means is provided with an edge engageable by said second end section of said blade member.

9. A speculum according to claim 1 wherein said arm section is displaced substantially radially relative to the axis of the pivoted connection of said blade member to said support member.

10. A speculum according to claim 1 wherein each of said first and second end sections of said blade member is disposed at an angle relative to said intermediate section thereof.

11. A speculum according to claim 1 wherein each of the first end sections of said blade members is provided with a portion curved in a plane including said centerline, cooperable with a comparable similar portion of a cooperating one of said blade members to provide a continuous curved surface when said first end sections of said blade members are disposed in engaging relationship.

12. A speculum according to claim 1 wherein each of the first end sections of said blade members is provided with an end portion configured to form a segment of a sphere.

13. A speculum according to claim 12 wherein said segment comprises an eighth segment of a sphere which when said first end portions of said blades are engaged together will provide a semispherical configuration facilitating the insertion of said blade members into said body cavity.

14. A speculum according to claim 1 including four of said blade members, equally circumferentially spaced about said centerline.

15. A speculum according to claim 1 wherein said means for releasably biasing said first end sections comprises a coil spring displaced coaxially relative to the pivoted connection of said blade member to said support member and interconnecting said blade member and said support member.

16. A speculum according to claim 1 wherein said means for releasably biasing said first end sections comprises an elastomeric o-ring encompassing portions of said blades.

17. A speculum according to claim 1 wherein at least the blade members thereof are formed of a metal.

18. A speculum according to claim 1 wherein at least the blade members are formed of a plastic material.

19. A speculum according to claim 1 wherein end portions of said first end sections cooperate to form a semispherical surface with one of said end sections intersecting said centerline, when said blade members are in a closed condition.

20. A speculum according to claim 19 wherein the edges of said first end sections are rounded.

21. A speculum according to claim 19 including at least three of said blade members with each of them including a first end section pivotal in a plane including said centerline, wherein end portions of said first end sections cooperate to form a semispherical surface with the other of said end sections intersecting said centerline, when said blade members are in a closed position.

22. A speculum according to claim 21 wherein the edges of said first end sections are rounded.

23. A speculum according to claim 19 wherein end portions of said first end sections cooperate to form a rounded surface with an opening at said centerline, when said blade members are in a closed condition.

24. A speculum according to claim 23 wherein the edges of said first end sections are rounded.

25. A speculum according to claim 19 including at least three of said blade members with each of them including a first end section pivotal in a plane including said centerline, wherein end portions of said first end portions cooperate to form a rounded surface with the other of said end sections having an opening at said centerline, when said blade members are in a closed condition.

26. A speculum according to claim 25 wherein the edges of said first end sections are rounded.

27. A speculum according to claim 1 including four blades each pivotal in a plane passing through said centerline, wherein when said blades are disposed in a closed condition, a first of said blades has a length greater than the other of said blades, an arcurate side surface extending not greater than 180° about said centerline and a free end curved toward said centerline, a second of said blades is disposed in diametrically opposed relation to said first blade and has a length shorter than said first blade, an arcuate side surface less than 180° about said centerline and a free end curved toward said centerline and third and fourth of said blades each is disposed between said first and second blades and has a length not greater than said second blade, an arcuate side surface length less than the arcuate side surface length of said second blade and a free end curved toward said centerline.

28. A speculum according to claim 27 wherein portions of said arcuate surfaces of said blades merge together when said blades are in a closed condition to provide a substantially continuous surface facilitating the insertion thereof into said cavity.

29. A speculum according to claim 27 wherein the edges of said blades are rounded.

30. A speculum according to claim 27 wherein portions of the side edges of said blades abut when in a closed condition.

31. A speculum according to claim 27 wherein the free ends of said second, third and fourth blades terminate a spaced distance from said centerline to provide an opening along said centerline when said blades are in a closed condition.

\* \* \* \* \*